United States Patent
Landis

[11] Patent Number: 5,615,414
[45] Date of Patent: Apr. 1, 1997

[54] SELF-CONFORMING VISOR APPARATUS

[75] Inventor: Timothy J. Landis, Loomis, Calif.

[73] Assignee: OP-D-OP, Inc., Roseville, Calif.

[21] Appl. No.: 396,411

[22] Filed: Feb. 27, 1995

[51] Int. Cl.$^6$ ................................................ A41D 20/00
[52] U.S. Cl. ........................ 2/12; 2/171; 2/195.2; 2/200.1
[58] Field of Search .................................... 2/10, 12, 171,
2/11, 15, 175.1, 181, 195.1, 195.2, 200.1,
200.2, 209.3

[56] References Cited

U.S. PATENT DOCUMENTS

| D. 206,191 | 11/1966 | Lawrence . | |
|---|---|---|---|
| 797,293 | 8/1905 | Lang et al. . | |
| 2,194,492 | 3/1940 | Bowers . | |
| 2,262,449 | 11/1941 | Buegeleisen . | |
| 2,603,784 | 7/1952 | Persons . | |
| 2,638,593 | 5/1953 | Eloranta . | |
| 2,829,374 | 4/1958 | Malcolm, Jr. . | |
| 3,555,562 | 1/1971 | Patton, Jr. . | |
| 3,868,727 | 4/1975 | Paschall . | |
| 4,117,553 | 10/1978 | Bay . | |
| 4,523,808 | 6/1985 | Miller et al. . | |
| 4,701,965 | 10/1987 | Landis . | |
| 4,850,049 | 7/1989 | Landis et al. . | |
| 4,852,186 | 8/1989 | Landis . | |
| 4,864,653 | 9/1989 | Landis . | |
| 4,955,087 | 9/1990 | Perez et al. | 2/12 |
| 4,964,171 | 10/1990 | Landis . | |
| 5,131,094 | 7/1992 | Ackerman | 2/12 |

Primary Examiner—Diana Biefeld
Attorney, Agent, or Firm—John P. O'Banion

[57] ABSTRACT

A self-conforming, head worn device which includes a head encircling band and a visor dependent therefrom which are fabricated from a flexible material that softens and conforms to a wearer's head upon warming up to the body temperature of the wearer. The head band includes a first fastening member on a first tail, and a second fastening member on a second tail of the head band. A plurality of protrusions on the first fastening member reversibly engage a plurality of bores on the second fastening member. The head band material is preferably a polymeric material which has a $T_g$ or softening temperature that is slightly lower than the human body temperature so that, when worn about the head of a wearer, the head band softens and conforms to the shape of the wearer's head, thereby maximizing wearer comfort. In an alternative embodiment, there is included hair receiving member in the form of a generally circular "pony-tail" adapter for use by persons with long hair.

13 Claims, 4 Drawing Sheets

SELF-CONFORMING VISOR APPARATUS

BACKGROUND OF THE INVENTION

1. Field of the Invention

This invention pertains to a head visor, and more particularly to a head visor that conforms to the shape of the head of the user, thereby providing greater wearing comfort.

2. Description of the Background Art

A variety of head visors, face shields, and visor-suspended masks are used for numerous purposes. Head visors having forwardly disposed bills are frequently employed to shade a wearer's eyes from sun or overhead room lights. Face shields in which the shield portion is suspended from a head visor are commonly used in laboratories, machine shops, and the like. In the medical, veterinary, and dental professions, implements such as lights, reflectors, magnifying optics, and protective shields are frequently suspended from head visors to aid the wearer while working. In many situations, the head visor cannot readily be adjusted or otherwise moved to make it more comfortable on the wearer's head because both of the wearer's hands are otherwise engaged. Particularly, surgeons, dentists, welders, and machinists are frequently involved in work that requires use of a head visor with shields or other equipment suspended therefrom, while at the same time both hands are fully occupied in complex, difficult, or dangerous procedures and cannot be freed to adjust the head visor for comfort.

Currently, head visors are adjusted on a user's head by a variety of means. For example, U.S. Pat. No. 4,964,171 discloses a protective shield and visor wherein a shield depends from the forward edge of a visor. U.S. Pat. No. 4,852,186 discloses a combined visor and protective shield supported by two bands which encircle a wearer's head. One band contains fasteners which snap fit into a row of spaced holes on the other band. By moving the fasteners to different holes, the bands can be adjusted to accommodate varying head sizes. U.S. Pat. No. 4,850,049 discloses a combined surgeon's cap, visor, and protective shield wherein a disposable surgeon's cap is attached to a visor with a protective shield depending therefrom. U.S. Pat. No. 4,864,653 discloses a protective shield and visor supporting same, wherein a visor is formed from a flat piece of sheet rubber having two tails provided with interfitting snaps which can be adjusted to accommodate the head size of the user. U.S. Pat. No. 4,701,965 discloses a visor-type mask for dentists wherein the visor is held onto a user's head by a pair of resilient curved bands. U.S. Pat. No. 4,523,808 discloses a welding helmet with auxiliary optical vision systems in which a welding helmet with a view port is suspended from a head band. U.S. Pat. No. 3,868,727 discloses a welding hood wherein a face shield attaches by snaps to a visor frame coupled to a head band. U.S. Pat. No. 3,555,562 discloses a face shield mounting having a band in a vertical plane over a user's head that can be adjusted by means of fitting studs into holes. U.S. Pat. No. 2,968,812 discloses eye-shields held onto a user's head by an encircling strap adjusted by buckles. U.S. Pat. No. 2,829,374 discloses a face shield and adjustable head band therefor in which the head band is fastened to a user's head by two flexible bands having a plurality of spaced holes that accommodate a button. U.S. Pat. No. 2,638,593 discloses a sun shield with depending visor that attaches to a user's head by two curved resilient bands. U.S. Pat. No. 2,603,784 discloses a night visor blackout glare device in which reversibly attachable shade portions may be coupled to a visor and head strap. U.S. Pat. No. 2,262,449 discloses a head windshield that is fastened onto a user's head by means of flexible straps which are adjusted by two buckles. U.S. Pat. No. 2,194,492 discloses a face and head protective devise held onto a user's head by two bands which may be adjusted and held in position by tension, using a wing-nut on a threaded bolt. U.S. Pat. No. 797,293 (1905) discloses a face shield secured to the user's head by an elastic band. U.S. Pat. No. D-206,191 discloses an eyeshade that is affixed to a user's head by means of two curved resilient bands.

As can be seen therefore, a variety of head visors and head gear have been devised for face and eye protection. However, the existing art is deficient in addressing the comfort of the wearer. Particularly, many visor devices are fabricated from generally rigid polymeric materials such as polystyrene, and are held onto the wearer's head by tension. This type of head visor rapidly becomes uncomfortable and requires frequent positional adjustment by the wearer. Further, visor devices which do provide adjustment means cannot be comfortably positioned because the head encircling portions are inherently uncomfortable to wear for prolonged periods. Because the aforementioned professions frequently prevent the wearer from adjusting head visors while working, the discomfort caused by currently available head visors can detract from the quality of the work performed in these professions.

Therefore, there is a need in these professions and others for a head visor which is comfortable to wear for extended periods of time without requiring readjustment or realignment on the wearer's head. The present invention satisfies this need, as well as others, and generally corrects the deficiencies found in the background art.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present inventions pertain to a self-conforming head worn visor apparatus which is comfortable to wear for prolonged periods of time without readjustment. In general terms, the invention comprises a head encircling band and a visor dependent therefrom which are fabricated from a flexible material that softens and conforms to a wearer's head upon warming up to the body temperature of the wearer.

By way of example and not of limitation, the head encircling band includes means for circumferential adjustment about a wearer's head, preferably in the form of a first fastening member on a first tail of the head band which includes a plurality of protrusions, and a second fastening member on a second tail of the head band which includes a plurality of apertures which are structured and configured to reversibly engage the protrusions on the first adjustment member in a snap fitting fashion. The head band material is preferably a polymeric material which has a $T_g$ or softening temperature that is slightly lower than the human body temperature so that, when worn about the head of a wearer, the head band softens and conforms to the shape of the wearer's head, thereby maximizing wearer comfort. In an alternative embodiment of the invention, there is included hair receiving means in the form of a generally circular "pony-tail" adapter for use by persons with long hair.

An object of the present invention is to provide a head visor which is comfortable to wear for extended periods of time without requiring readjustment or realignment of the visor.

Another object of the present invention is to provide a head visor which includes a head-conforming member made of material which, softens and conforms to the shape of the wearer's head upon warming.

Another object of the present invention is to provide a head visor which can be quickly and easily adjusted to fit about a wearer's head.

Another object of the present invention is to provide a head visor which allows a wearer's hair to be held away from the wearer's face in a comfortable fashion.

Another object of the present invention is to provide a head visor which is suitable for attachment or suspension of face shields, lights, reflectors, magnifying optics, or other equipment from the visor.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more particularly to the drawings, for illustrative purposes the present invention is embodied in the head worn visor apparatus 10 which is generally shown in FIG. 1 through FIG. 5. It will be appreciated that the apparatus may vary as to configuration and as to details without departing from the basic concepts as disclosed herein.

Figure 1:
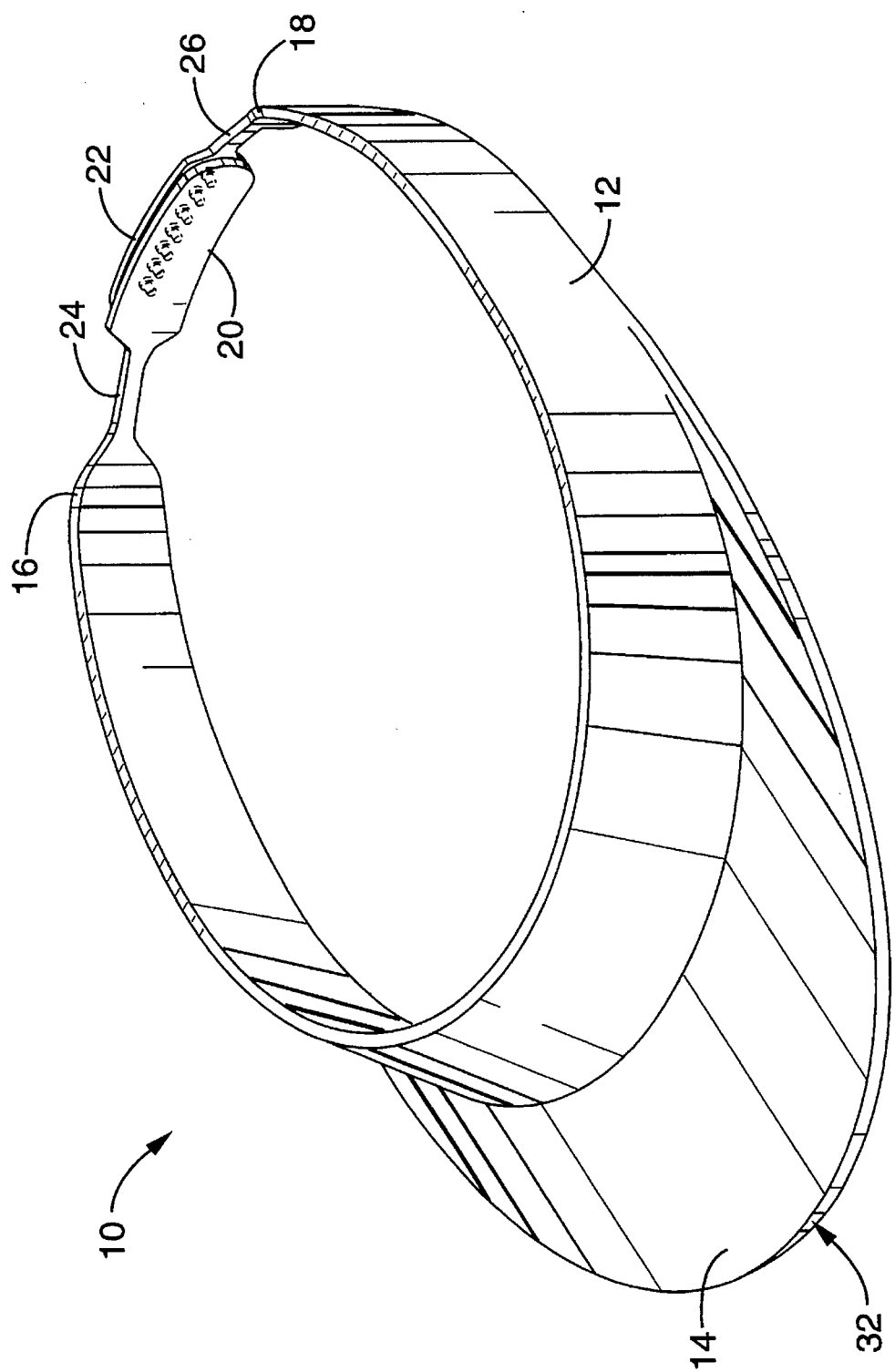
FIG. 1 is a perspective view of a visor apparatus in accordance with the present invention.
Figure 2:
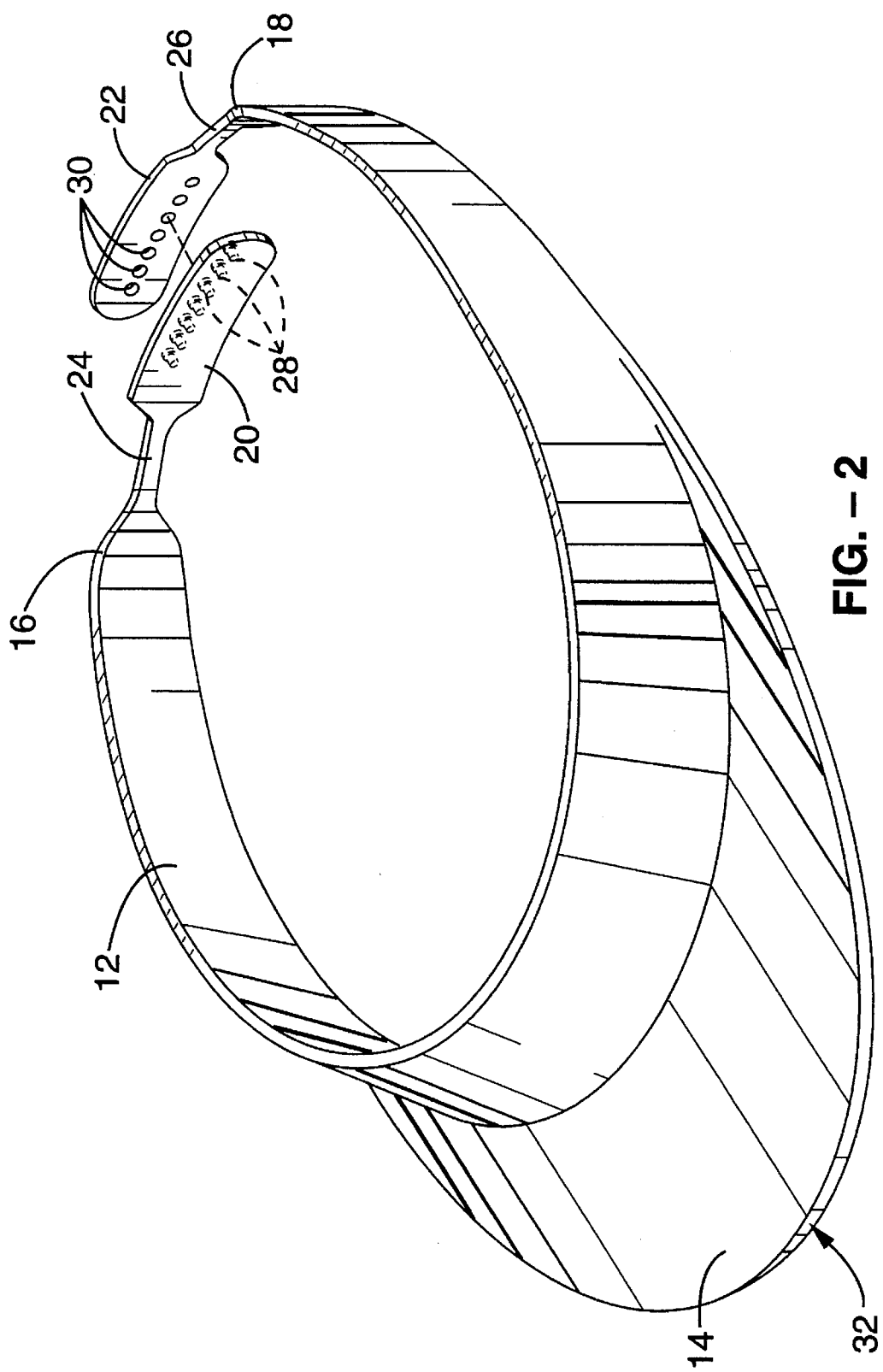
FIG. 2 is a perspective view of the apparatus shown in FIG. 1 with first and second fastening members disengaged relative to each other.

FIG. 1 and FIG. 2 illustrate generally the head worn visor apparatus 10 which comprises the present invention. The apparatus includes a head encircling band 12 and a visor 14 which depends from the front of head band 12. Head band 12 also includes a first tail 16 and a second tail 18, as well as circumferential adjustment means, preferably in the form of a first fastening member 20 and a second fastening member 22. First fastening member 20 is coupled to first tail 16 by a thin connecting portion 24, and second fastening member 22 is coupled to second tail by a similar thin connecting portion 26. First fastening member 20 includes a plurality of protrusions or nipples 28, and second fastening member 22 includes a plurality of apertures or bores 30 which are structured and configured to reversibly engage protrusions 28 by snap fitting. Other circumferential adjustment means are also contemplated for use with the present invention, including buttons, snap fasteners, fastening hook and pile fabric arrangements such as Velcro®, and like adjustable fastening means, which would be used with the present invention in association with first and second tails 16, 18.

The apparatus is preferably fabricated as a single unit, by molding or the like. The material used has a glass transition temperature $T_g$ or a softening temperature that is equal to or slightly below the human body temperature, so that when worn on the head of a wearer, head band 12 softens and conforms to the shape of the wearer's head, thereby maximizing the wearer's comfort. Preferably, the $T_g$ or softening temperature of materials used in the present invention will be in the range of between about 95° and 99° Fahrenheit, for use at ambient temperatures generally found in offices, laboratories, or dental or surgical suites. It is contemplated, however, that slightly lower softening temperature materials may be employed if the apparatus is to be worn in lower temperature environments. Similarly, where the invention is to be used in higher temperature environments, the material used could be of a higher softening temperature. Several materials are contemplated for use with the present invention. For example, polypropylene of suitable ductility and polyethylene of suitable density will have the correct thermal properties for use with the present invention. Additionally, many polymers can have their $T_g$ or softening temperature lowered by addition of suitable plasticizers, so that materials having a $T_g$ which is too high for use with the present invention may be modified by addition of a plasticizer to move the $T_g$ into the optimum temperature range. Treatment of polyvinyl chloride with the plasticizer di-octyl phthalate is one possible example. Further, acrylic monomers which tend to form high $T_g$ homopolymer glasses such as methyl methacrylate can be co-polymerized with acrylic monomers which as homopolymers form low $T_g$ rubbery material, such as n-butyl methacrylate. A monomer ratio in the copolymer can be obtained which produces a material with the desired $T_g$ for use with the present invention. Thus, several man-made polymeric materials may be used with the present invention.

Since visor 14 projects away from the wearer's head, only the portion adjacent the wearer will soften and conform to the wearer's head. The bill or brim 32 of visor 14 is sufficiently distant from the wearer that brim 32 will remain rigid, allowing attachment of face shields and the like thereto. Alternatively, visor 14 could be fabricated from a different material which not soften at the temperature which material of head band 12 softens, with visor 14 then attached to head band by adhesive or other fastening means commonly used in the art. In situations where the invention will be used in warm environments or in direct sunlight, using a visor made from material with a higher $T_g$ than that of head band 12 will be preferred.

In use, the apparatus is fitted to the head of a wearer by adjusting first and second fastening members 20, 22 to the circumference of the wearer's head, and snapping protrusions 28 in apertures 30. As the head band 12 is in contact with the wearer's head and approaches the wearer's body temperature, its shape will conform to the shape of the wearer's head.

Figure 3:
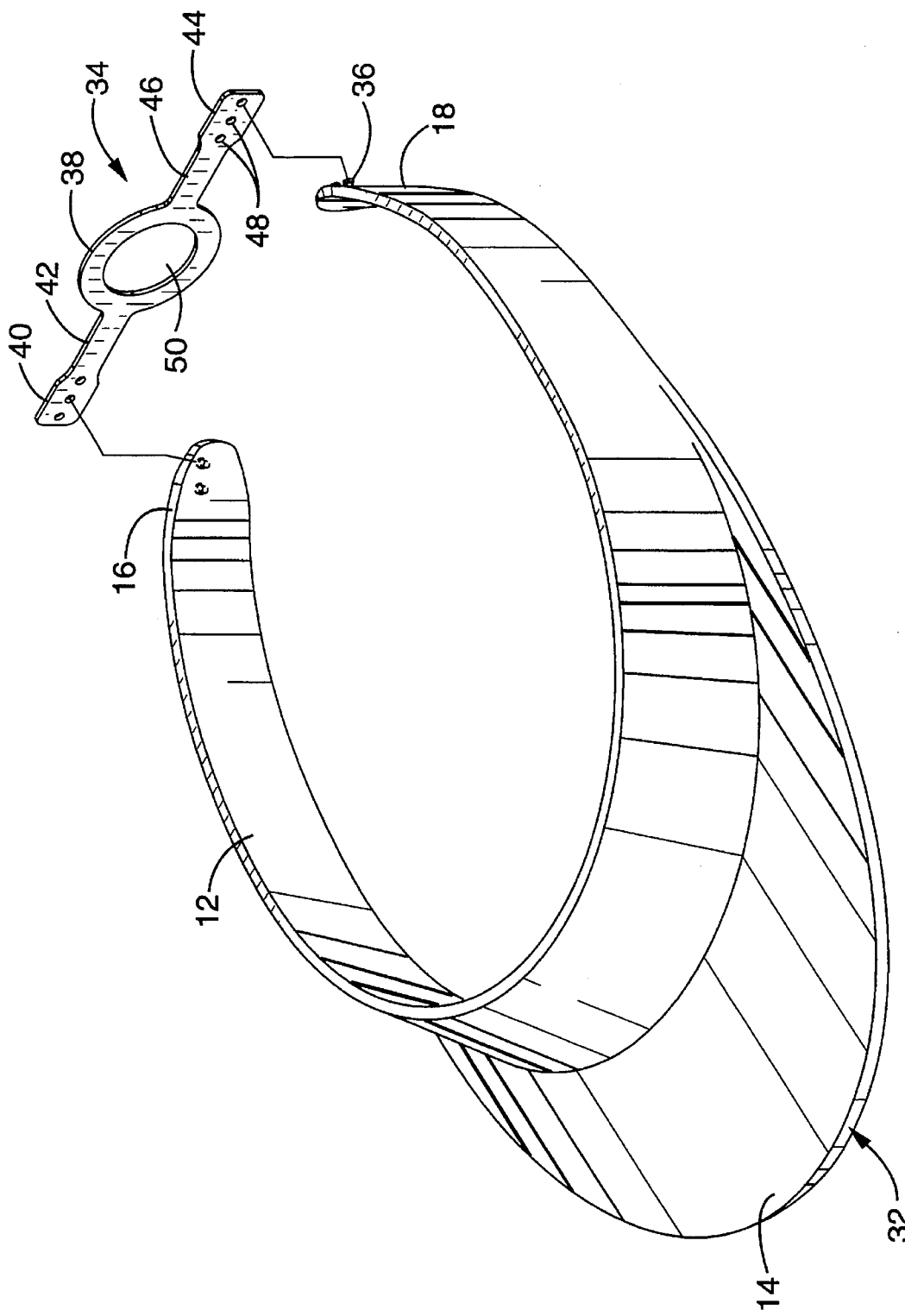
FIG. 3 is an exploded perspective view an alternative embodiment of the apparatus shown in FIG. 1.
Figures 4, 5:
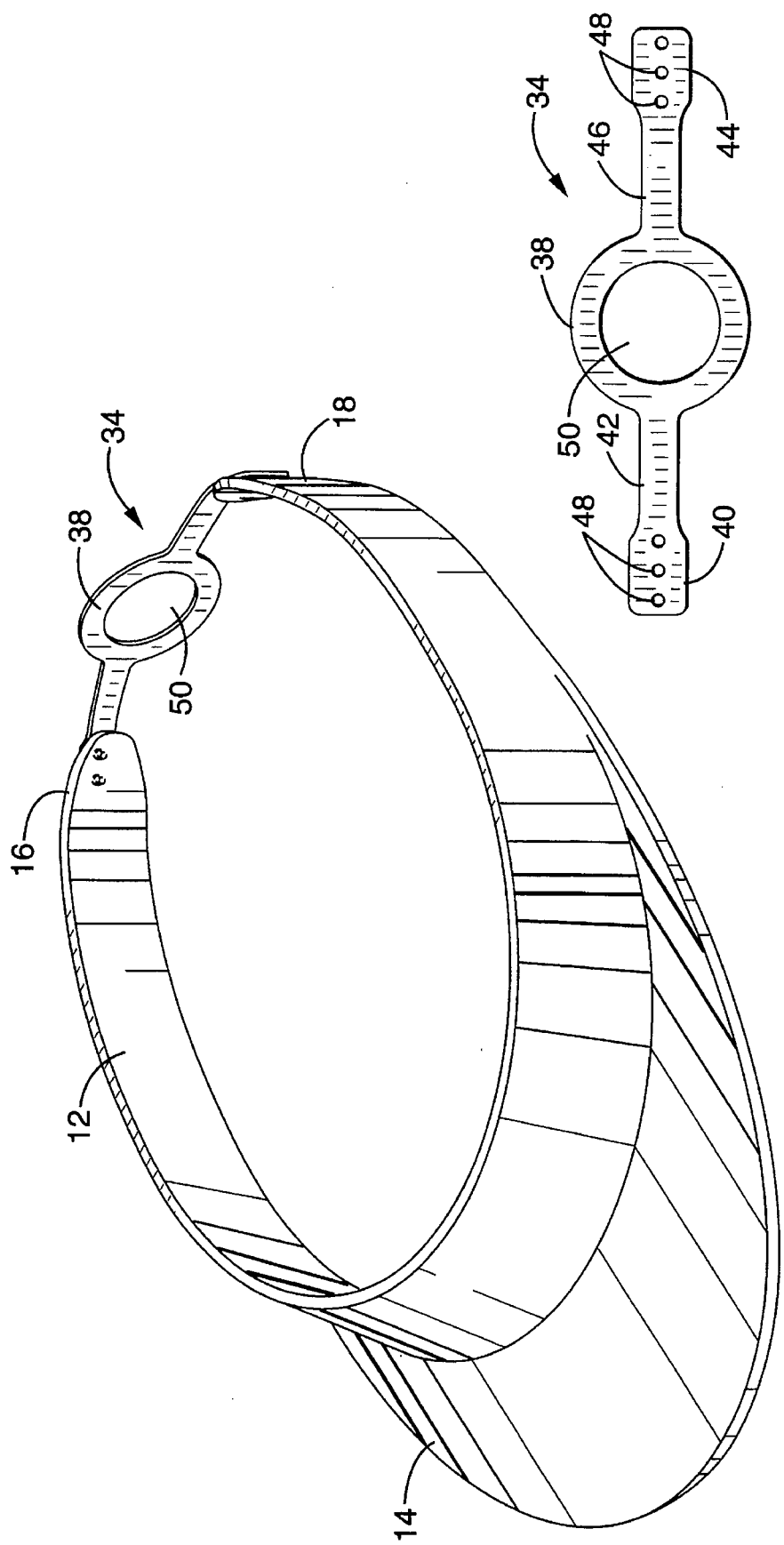
FIG. 4 is an assembled view of the apparatus shown in FIG. 3.
FIG. 5 shows an exemplary hair receiving member for use with the embodiment of the head visor shown in FIG. 3 and FIG. 4

Referring now to FIG. 3 through FIG. 5, an alternative embodiment of the present invention is generally shown, wherein like reference numerals denote like parts. Persons having long hair frequently tie it in a "pony tail" or similar arrangement at the back of their heads while they are working. The embodiment shown therein is designed to accommodate such long hair arrangements, and includes a hair receiving means, preferably in the form of hair-receiving member 34, and means for adjustably attaching hair-receiving member 34 to head band 12. As with the first embodiment, a visor 14 depends from a head band 12, with head band 12 including a first tail 16 and a second tail 18. The adjustment means includes a plurality of protrusions 36 on first and second tails 16, 18. Hair-receiving member 34 includes an annular ring portion 38. The adjustment means further comprises means for connecting to hair receiving member, preferably in the form of a first connecting member 40 attached to annular ring 38 by strap 42, and a second connecting member 44 attached to annular ring by strap 46. First and second connecting members 40, 44 each include a plurality of apertures 48 which are structured and configured to reversibly engage protrusions 36 on first and second tails, preferably by snap fitting. Those skilled in the art will appreciate that apertures 48 could alternatively be located on tails 16, 18 with corresponding apertures located on connecting members 40, 44. Also, other fasteners such as Velcro®, buttons, or the like could be used if desired.

The alternative embodiment of the present invention shown in FIG. 3 through FIG. 5 is used in generally the same manner as the first embodiment related above. The wearer fits his or her hair through opening 50 in annular ring 38 of the hair receiving member 34, and positions first and second connecting members 40, 44 with first and second tails 16, 18 according to the circumference of the wearer's head. First and second connecting members 40, 44 are coupled to first and second tails 16, 18 on head band 12 by engaging protrusions 36 in apertures 48. Preferably, hair receiving member 34 is made of the same material as head band 12, and will conform to the shape of the wearer's head in the same manner as head band 12.

Accordingly, it will be seen that this invention provides a head visor which provides for quick, easy, accurate adjustment at three points about the circumference of a wearer's head, which can conform comfortably to the wearer's head, and which can accommodate wearer's long hair. Although the description above contains many specificities, these should not be construed as limiting the scope of the invention but as merely providing illustrations of some of the presently preferred embodiments of this invention. Thus, the scope of this invention should be determined by the appended claims and their legal equivalents.

I claim:

1. A visor apparatus, comprising:
   (a) a head band, said head band including a first tail and a second tail;
   (b) said head band and said tails fabricated from a polymeric material having a softening temperature of between approximately 90° and 105° Fahrenheit;
   (c) a visor, said visor depending from said head band; and
   (d) adjusting means for circumferentially adjusting said head band about a wearer's head.

2. An apparatus according to claim 1, wherein said adjusting means further comprises:
   (a) a first fastening member, said first fastening member coupled to said first tail of said head band, said first fastening member including a plurality of protrusions; and
   (b) a second fastening member, said second fastening member coupled to said second tail of said head band, said second tail including a plurality of apertures, said apertures structured and configured to reversibly engage said protrusions on said first fastening member.

3. An apparatus according to claim 2, wherein said visor is fabricated from a material having a softening temperature of between approximately 90° and 105° Fahrenheit.

4. A head visor according to claim 3, wherein said head band and said visor are made of polypropylene.

5. A head visor according to claim 1, further comprising hair receiving means for receiving hair of a wearer.

6. A head visor according to claim 5, wherein said hair receiving means comprises a hair receiving member, said hair receiving member having an annular ring, said ring including an opening.

7. A head visor according to claim 6, wherein said adjusting means comprises:
   (a) a plurality of protrusions on said first tail of said head band;
   (b) a plurality of protrusions on said second tail of said head band;
   (c) a first coupling member, said first coupling member attached to said ring on said hair receiving member, said first coupling member including a plurality of apertures, said apertures structured and configured to reversibly engage said protrusions on said first tail; and
   (d) a second coupling member, said second coupling member attached to said ring on said hair receiving member, said second coupling member including a plurality of apertures, said apertures structured and configured to reversibly engage said protrusions on said second tail.

8. An apparatus according to claim 7, wherein said visor is fabricated from a material having a softening temperature of between approximately 90° and 105° Fahrenheit.

9. A head visor according to claim 8, wherein said head band and said visor are made of polypropylene.

10. A visor apparatus, comprising:
    (a) a head band, said head band including a first tail and a second tail;
    (b) said head band and said tails fabricated from a polymeric material having a softening temperature of between approximately 90° and 105° Fahrenheit;
    (c) a visor, said visor depending from said head band;
    (d) said visor fabricated from a polymeric material having a softening temperature of between approximately 90° and 105° Fahrenheit;
    (e) a first fastening member, said fastening member coupled to said first tail of said head band, said first fastening member including a plurality of protrusions; and
    (f) a second fastening member, said second fastening member coupled to said second tail of said head band, said second fastening member including a plurality of apertures, said apertures structured and configured to reversibly engage said protrusions on said first fastening member.

11. An apparatus according to claim 10, wherein said head band and said visor are made of polypropylene.

12. A visor apparatus, comprising:
    (a) a head band, said head band including a first tail and a second tail, said head band and said tails fabricated from a polymeric material having a softening temperature of between approximately 90° and 105° Fahrenheit;
    (b) a visor depending from said head band, said visor fabricated from a polymeric material having a softening temperature of approximately 90° and 105° Fahrenheit;

(c) a hair receiving member, said hair receiving member having an annular ring, said ring including an opening;

(d) a plurality of protrusions on said first tail;

(e) a plurality of protrusions on said second tail;

(f) a first coupling member, said first coupling member attached to said ring on said hair receiving member, said first coupling member including a plurality of apertures, said apertures structured and configured to reversibly engage said protrusions on said first tail; and (g) a second coupling member, said second coupling member attached to said ring on said hair receiving member, said second coupling member including a plurality of apertures, said apertures structured and configured to reversibly engage said protrusions on said second tail.

13. An apparatus according to claim 12, wherein said head band and said visor are made of polypropylene.

\* \* \* \* \*